US00PP28934P3

(12) United States Plant Patent
Stephens

(10) Patent No.: US PP28,934 P3
(45) Date of Patent: Feb. 6, 2018

(54) RASPBERRY PLANT NAMED 'NN08002'

(50) Latin Name: ***Rubus idaeus* L.**
Varietal Denomination: NN08002

(71) Applicant: Pacific Berries LLC, Lynden, WA (US)

(72) Inventor: Joseph Stephens, Auckland (NZ)

(73) Assignee: Pacific Berries LLC, Lynden, WA (US)

( * ) Notice: Subject to any disclaimer, the term of this patent is extended or adjusted under 35 U.S.C. 154(b) by 0 days.

(21) Appl. No.: 15/530,013

(22) Filed: Nov. 18, 2016

(65) Prior Publication Data

US 2017/0172037 P1 Jun. 15, 2017

Related U.S. Application Data

(60) Provisional application No. 62/266,306, filed on Dec. 11, 2015.

(51) Int. Cl.
*A01H 5/08* (2006.01)

(52) U.S. Cl.
USPC ..... Plt./204

(58) Field of Classification Search
USPC ..... Plt./304
See application file for complete search history.

*Primary Examiner* — Annette H Para
(74) *Attorney, Agent, or Firm* — Lathrop & Gage LLP

(57) ABSTRACT

A new and distinct floricane fruiting red raspberry, *Rubus idaeus* L., variety is described. The variety results from selection among a population of seedlings derived from a controlled cross between 'Wakefield' (seed parent) (U.S. Plant Pat. No. 21,185) and 'NR14' (pollen parent) (not patented). The new variety is distinguished from others by large, very firm fruit that have a medium red skin colour, and ripen midseason. Fruit of the new variety appears very suitable for machine harvesting and the process fruit market.

4 Drawing Sheets

Genus and species plant claimed: *Rubus idaeus* L.
Variety denomination: 'NN08002'.

BACKGROUND OF THE INVENTION

The new variety of red raspberry, *Rubus idaeus* L., was created in the course of a planned breeding program carried out at Lynden, Washington State, USA. It was selected from a population of seedlings derived from a controlled cross carried out in 2006 between 'Wakefield' (seed parent) (U.S. Plant Pat. No. 21,185) and 'NR14' (pollen parent) (not patented). The original plant of the new variety was selected in 2008 for suitability for machine harvesting and for process markets. In 2010, 'NN08002' was asexually propagated by tissue culture. The resulting plants were planted at Lynden, Wash., USA and were subsequently found to be true to type demonstrating that the characteristics of the new variety, 'NN08002', are stable and transmitted without change through succeeding generations.

SUMMARY OF THE INVENTION

'NN08002' is characterised by large, very firm, red fruit suitable for machine harvesting and for processing.

'NN08002' is distinguished from a number of varieties by the following characteristics:

When compared to 'Meeker', 'NN08002' fruit has lighter red skin colour, larger size and is firmer.

When compared to 'Wakefield', 'NN08002' fruit has lighter red skin colour, larger size and begins ripening earlier.

When compared to 'NR14', 'NN08002' fruit is firmer and larger in size.

BRIEF DESCRIPTION OF THE DRAWINGS

The accompanying photographs show typical specimens of the plant, fruit, and leaves of the new variety was depicted in colours as nearly true as is reasonably possible to make the same colour in illustrations of this character.

DETAILED BOTANICAL DESCRIPTION

Figure 1:
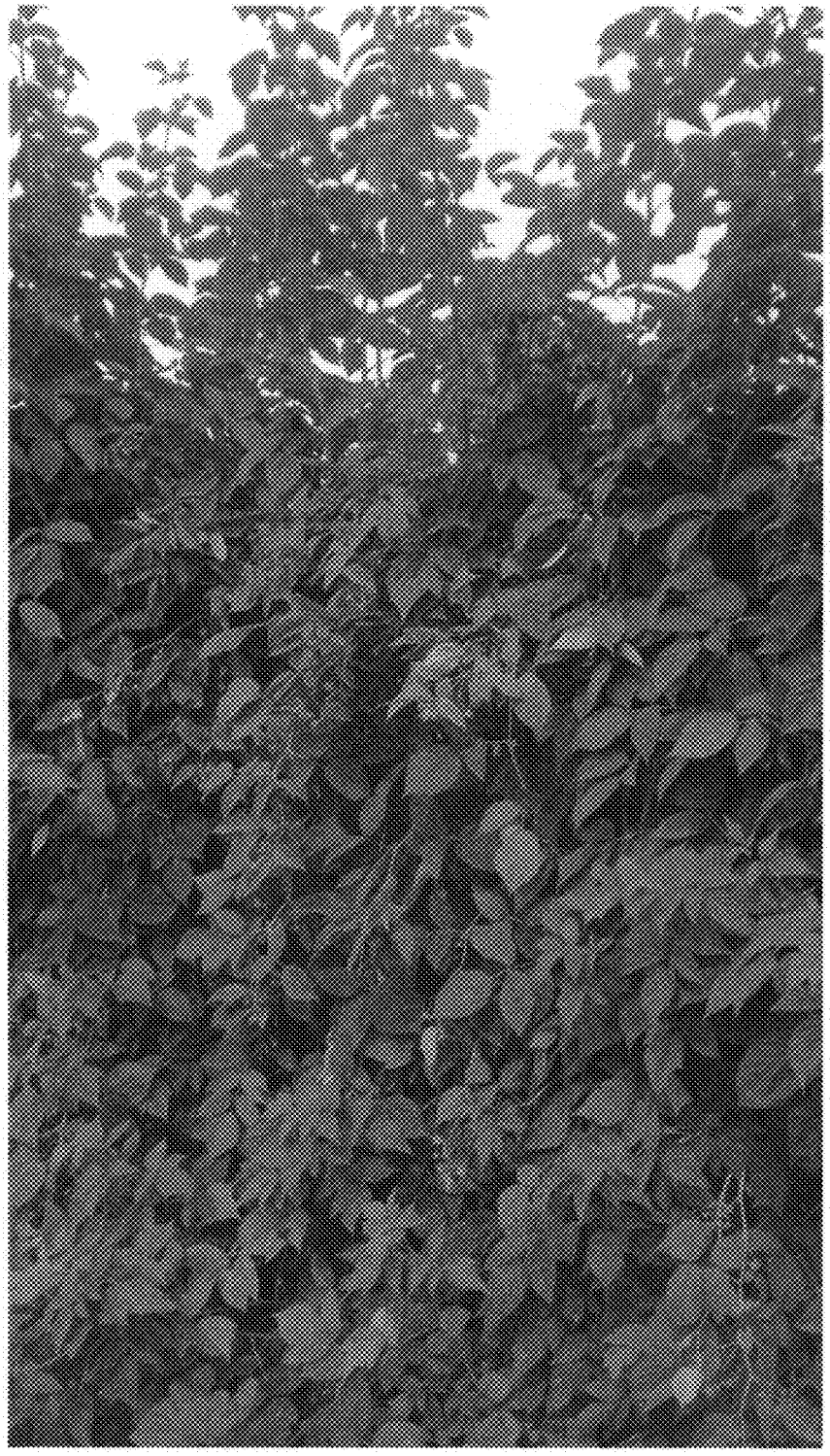
FIG. 1: 'NN08002' three year old plant.
Figure 2:
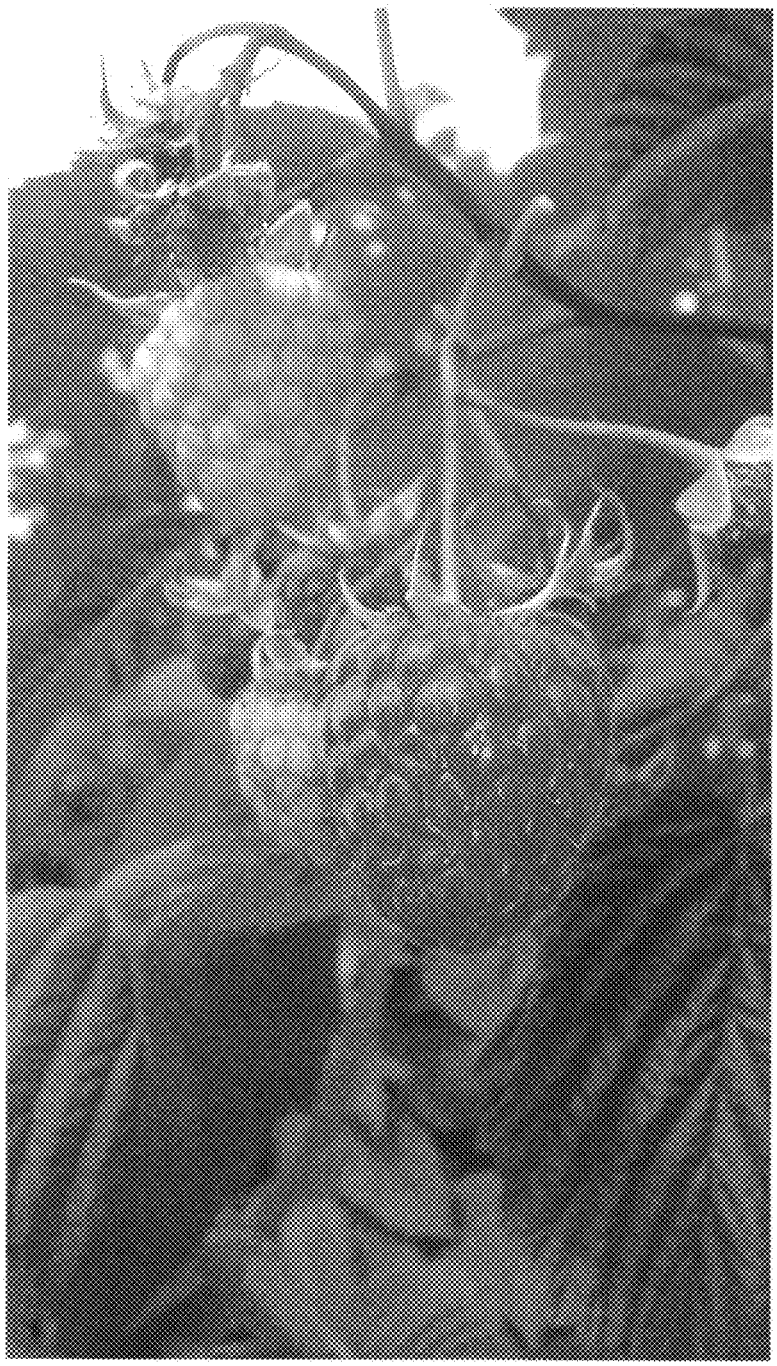
FIG. 2: 'NN08002' fruit on bush.
Figure 3:
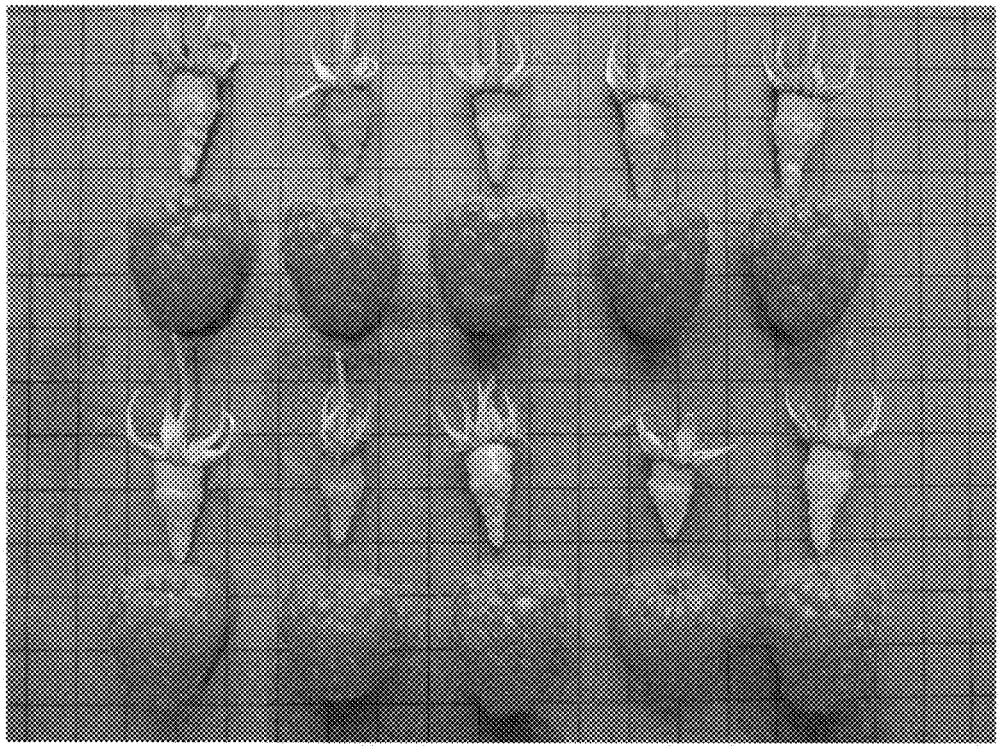
FIG. 3: Mature 'NN08002' fruit and receptable.
Figure 4:
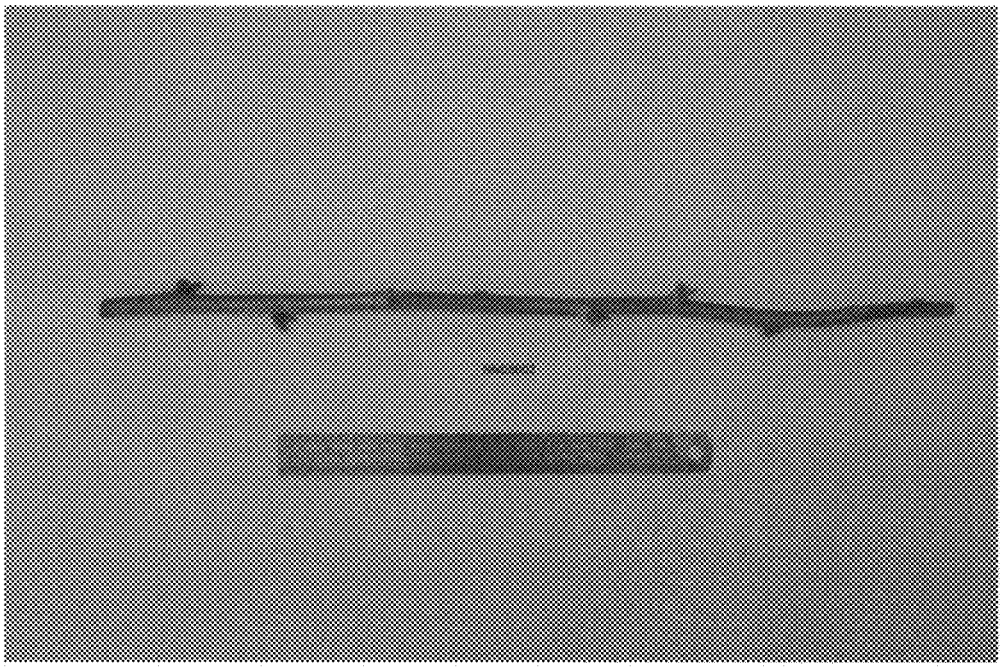
FIG. 4: 'NN08002' primocane.
Figure 5:
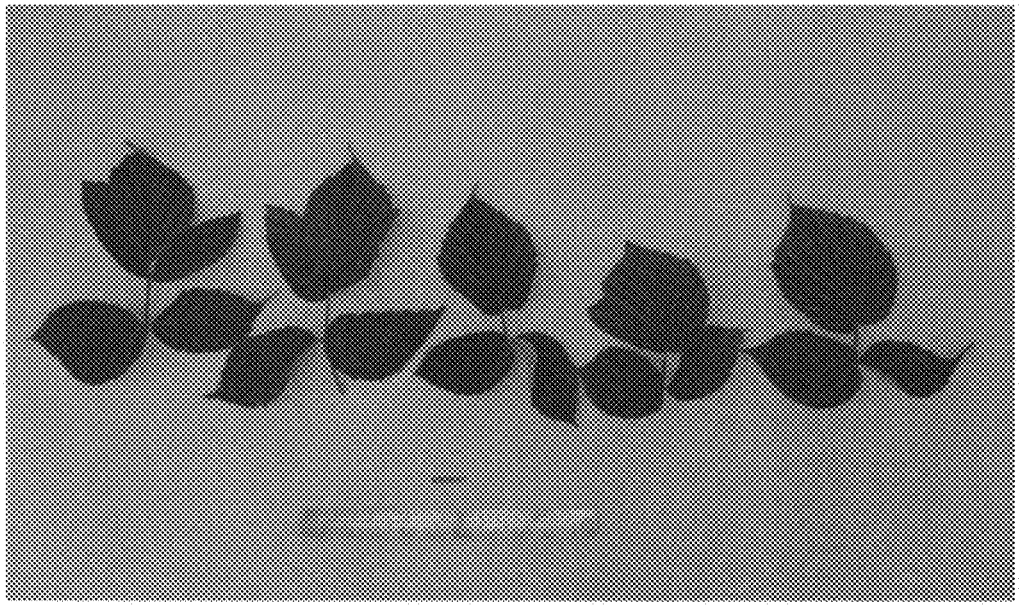
FIG. 5: 'NN08002' upper surface of leaf.

Horticultural terminology is used in accordance with UPOV guidelines for raspberry. All dimensions are in millimeters, weights in grams (unless otherwise stated). Where a color reference is given these refer to The R.H.S. Color Chart, The Royal Horticultural Society, London. 4th Edition, 2001. The specimens described were grown in Lynden, Washington State, USA. The plants were 3 years old.

Environmental data for the Lynden, Wash., USA growing area demonstrates conditions in spring and early summer (equating to the harvest period for the variety) as follows:

Spring (April/May); mean daily temperature in the range 10-11° C. (mean daily minimum 5.5° C., mean daily maximum 15.5° C.).

Early summer (June/July); mean daily temperature 16° C. (mean daily minimum 10° C., mean daily maximum 21.5° C.).

In winter temperatures below 0° C. are common, the daily mean for December/January is 2.5° C. with the lowest temperature unlikely to be colder than −13° C. Average annual rainfall is approximately 1500 mm.

Flower description:

*Plant and foliage*.—Plants exhibit a strong upright growth habit. Average cane length was approximately 242 cm with an average of 35 nodes per cane and an internode average length of 12 mm. The average diameter of the canes at 1-1.5 m height was 10 mm. Spines were present with an approximate density of 31 per cm of cane less than 30 cm from the base and near the tip approximately 1 per cm. In the centre region of the canes spines were sparse. The colour of the spines was near greyed purple 187B with average size of base of spine 0.9 mm and average length 0.6 mm. Cane pubescence (controlled by what is known as gene H) was absent and canes have very little cane bloom. The colour of the mature cane on the sunny side was near greyed purple 183C and on the shady side near yellow green 145A. The average length of leaf axil buds after harvest was 6 mm. Young shoots were erect in attitude and were near yellow green 144A and B in colour. There was no anthocyanin coloration of the growing tip. Both three and five leaflets were present. The terminal leaflet shape of the apex was pointed and the shape of the base was cordate. The shape of the leaf upper side in cross section was flat to convex. The upper side of the leaf was moderately glossy with few hairs with moderately strong puckering. Average total leaf length was 24 cm, average total leaf width was 21 cm, average terminal leaflet length was 11 cm and average terminal leaflet width was 7 cm. Leaf color on the upper side was near green 137A and lower side was near grey-green 194A. The leaf margin was serrate. There was pronounced leaf venation and the vein coloration was near yellow green 145B. Average leaf petiole length was 8 mm and average diameter was 3 mm. Petiole color was near yellow green 145B with anthocyanin coloration on the upper side near grey-purple 183A. Hairs were present on the petioles.

*Infloresence*.—Flowers were arranged in a paniculate inflorescence. Average pedicel length was 18 mm and average width was 1 mm. Moderate anthocyanin coloration was found on the sunny side of the pedicel, near red-purple 59A and on the shady side the color was near yellow green 144A. Spines were present on the pedicel with approximately 2 per pedicel. Average spine length was 1.4 mm and diameter 0.8 mm. Average peduncle length was 14 mm and average diameter 1.3 mm. The color of the peduncle near the top was red-purple 59A and near the base yellow green 144A. Flowers had five sepals and were near grey green, 194A on the outer sepal and near the base the color was near yellow green 144A. Average sepal length was 12 mm. Average diameter of the terminal flower was 8.1 mm. Five petals were present and average petal length was 7.4 mm and average width 3.6 mm. The petal shape was vase, the shape of the tip moderately pointed and the shape of the base flat. The petals had moderate venation and the margins were smooth. The primary color of the petals was white 155C. Flowers contained an average of 93 stamens and average length of the stamen filament was 4 mm. The color of the stamens and filament was near white 155C. The anthers was approximately 0.6 mm in length and near grey brown, 199A in color. Approximately 81 stigma were present per flower and the color of the stigma was near yellow green 145C. Flower fragrance was absent.

Fruit:

*Fruit*.—Fruit was produced on previous year's cane in summer. Fruit was conical in shape and average berry weight was 4.8 g, average length 23.7 mm and average width 20.9 mm. Fruit had a long pointed receptable which had an average length of 16 mm and average width of 7 mm. Fruit skin color and flesh color was near red purple, 59A. Skin had medium glossiness and hairs were present. The width of an average single druplet was 4 mm. Approximately 80 seeds were present per fruit. The average seed weight was 0.16 g and when dry had a near greyed orange 164D and N170D color. Average seed length was 2.8 mm and average width 1.5 mm. Fruit was firm and the fruiting lateral had a dropping habit. Soluble solids concentration averaged 10.2° Brix.

*Harvest*.—'NN08002' fruit is harvested mid-season and begins ripening earlier than 'Wakefield' and around the same time as 'Meeker'. It is very suitable for harvest by machine due to the ease with which fruit dislodges from the receptacle. Fruit is firm and well suited to individually quick frozen (IQF) operations. The red color of the fruit means it is also suitable for other types of processing markets. In machine harvested trials in the Pacific North West, USA, the average fruit yield over several seasons was 6.9 t/acre.

*Pest and disease resistance*.—'NN08002' has tested negative to numerous RBDV tests using enzyme-linked immunosorbent assay (ELISA) and no RBDV symptoms have been seen in the field on plants resulting in the conclusion that 'NN08002' is likely to be resistant to RBDV found in the USA. In field trials in the Pacific North West, USA, 'NN08002' appears to have some tolerance to root rot caused by *Phytophthora rubi*.

*Geographical adaption*.—Observations indicate that the variety is well-suited to production in regions that offer a medium-high amount of winter chill, for example, 'NN08002' performs well in USDA Plant Hardiness zones 8-10 (published as the 2003 US National Arboretum "Web Version" of the USDA Plant Hardiness Zone Map USDA Miscellaneous Publication No. 1475, Issued January 1990).

I claim:

1. A new and distinct raspberry plant substantially as illustrated and described herein.

* * * * *